United States Patent [19]

Oohata et al.

[11] Patent Number: 5,187,195

[45] Date of Patent: Feb. 16, 1993

[54] ANTHRAQUINONE DERIVATIVES AND PREPARATION THEREOF

[75] Inventors: Nobutaka Oohata; Motoaki Nishikawa; Sumio Kiyoto, all of Tsukuba; Shigehiro Takase, Ishioka; Keiji Hemmi, Tsukuba; Hidetsugu Murai, Tsukuba; Masakuni Okuhara, Tsukuba, all of Japan

[73] Assignee: Fujisawa Pharmaceutical Co., Ltd., Osaka, Japan

[21] Appl. No.: 543,437

[22] Filed: Jun. 26, 1990

[30] Foreign Application Priority Data

Jun. 30, 1989 [GB] United Kingdom ............... 8915110
Oct. 23, 1989 [GB] United Kingdom ............... 8923848

[51] Int. Cl.$^5$ .................... A01N 37/00; A01N 35/04; C07C 50/22
[52] U.S. Cl. .................... 514/510; 514/680; 514/686; 514/929; 552/220; 552/296; 552/298
[58] Field of Search .............. 552/220, 296, 298; 514/510, 680, 686, 929

[56] References Cited

U.S. PATENT DOCUMENTS 3,721,684  3/1973  Meyers et al. ............ 552/220
4,215,062  7/1980  Mitscher ................. 552/220
4,681,584  7/1987  Gale et al. .............. 604/894

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

Anthraquinone compounds of the formula:

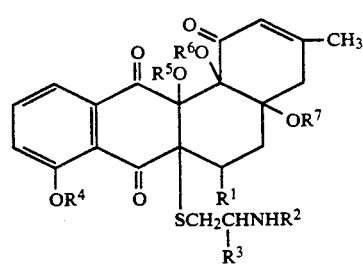

wherein:
$R^1$ is hydrogen, hydroxy or acyloxy,
$R^2$ is hydrogen or acyl,
$R^3$ is acyl,
$R^4$ is hydrogen or acyl,
$R^5$ is hydrogen or acyl,
$R^6$ is hydrogen or acyl, and
$R^7$ is hydrogen or acyl have been found to possess endothelin antagonistic properties and are producible by various synthetic and fermentation processes.

13 Claims, No Drawings

ANTHRAQUINONE DERIVATIVES AND PREPARATION THEREOF

This invention relates to new compounds having a biological activity. More particularly, this invention relates to new biologically active ANTHRAQUINONE DERIVATIVES, which have endothelin antagonistic activity, to processes for their preparation, and to pharmaceutical compositions comprising the same.

ANTHRAQUINONE DERIVATIVES of this invention have a following general formula

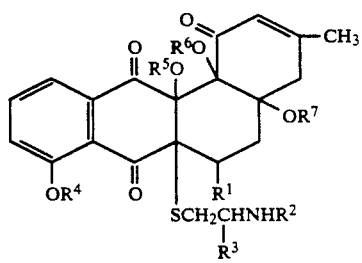

[I]

wherein
$R^1$ is hydrogen, hydroxy or acyloxy,
$R^2$ is hydrogen or acyl,
$R^3$ is acyl,
$R^4$ is hydrogen or acyl,
$R^5$ is hydrogen or acyl,
$R^6$ is hydrogen or acyl, and
$R^7$ is hydrogen or acyl.

Among ANTHRAQUINONE DERIVATIVES, the compound in which $R^1$ is hydrogen, $R^2$ is acetyl, $R^3$ is carboxy, $R^4$ is hydrogen, $R^5$ is hydrogen, $R^6$ is hydrogen and $R^7$ is hydrogen (hereinafter referred to as FR901366 substance), and the compound in which $R^1$ is hydroxy, $R^2$ is acetyl, $R^3$ is carboxy, $R^4$ is hydrogen, $R^5$ is hydrogen, $R^6$ is hydrogen and $R^7$ is hydrogen (hereinafter referred to as FR901367 substance) can be produced by fermentation process using a strain capable of producing FR901366 substance and/or FR901367 substance and belonging to the genus Streptomyces such as Streptomyces sp. No. 89009 in a nutrient medium.

The fermentation process is explained in detail in the following.

(1) Microorganism

Particulars of the microorganism used for producing FR901366 substance and/or FR901367 substance are explained in the following.

The microorganism which can be used for the production of FR901366 substance and/or FR901367 substance is a strain belonging to the genus Streptomyces which is capable to produce FR901366 substance and/or FR901367 substance, among which Streptomyces sp. No. 89009 was isolated from a soil sample collected at Narita-shi, Chiba-ken, Japan.

A lyophilized sample of the newly isolated Streptomyces sp. No. 89009 was deposited with the Fermentation Research Institute, Agency of Industrial Science and Technology (1-3, Higashi 1 chome, Tsukuba-shi, Ibaraki-ken, 305 Japan) under the accession number of FERM BP-2474 (deposited date: 14 June, 1989).

It is to be understood that the production of the novel FR901366 substance and/or FR901367 substance is not limited to the use of the particular organism described herein, which is given for the illustrative purpose only. This invention also includes the use of any mutants which are capable of producing FR901366 substance and/or FR901367 substance including natural mutants as well as artificial mutants which can be produced from the described organism by conventional means such as irradiation of X-ray, ultra-violet radiation, treatment which N-methyl-N'-nitro-N-nitrosoguanidine, 2-aminopurine, and the like.

Characteristics of Streptomyces sp. No. 89009:

The Streptomyces sp. No. 89009 has the following morphological, cultural, biological and physiological characteristics.

(i) Morphological Characteristics

The methods described by Shirling and Gottlieb 1) were employed for this taxonomic study.

Morphological observations were made with light and electron microscopes on cultures grown at 30° C. for 14 days on oatmeal agar, yeast extract-malt extract agar and inorganic salts-starch agar.

The vegetative mycelium developed well without fragmentation. The aerial mycelium branched monopodially and formed spiral chains and rectus-flexibilis chains of spores with more than 30 spores per chain. The spores had a smooth surface and were oval in shape with a size of 0.5–0.8 ×0.7–1.0 μm. Sclerotic granules, sporangia and zoospores were not observed.

(ii) Cultural Characteristics

Cultural characteristics were observed on the described by Shirling and Gottlieb as mentioned above, and by Waksman[2]).

The incubation was carried out at 30° C. for 21 days. The color names used in this study were taken from Methuen Handbook of Colour[3]). The results are shown in Table 1.

TABLE 1

Cultural characteristics of the strain No. 89009

| Medium | Cultural characteristics |
|---|---|
| yeast extract-malt extract agar | G: good |
| | A: abundant, brownish gray(8E2) to black |
| | R: violet brown(11F6) |
| | S: none |
| oatmeal agar | G: good |
| | A: abundant, brownish gray (9E2, 9F2) |
| | R: reddish brown(9E7) |
| | S: pale pink |
| inorganic salts-starch agar | G: good |
| | A: abundant, brownish gray(7E2) to black |
| | R: grayish orange(6B5) |
| | S: none |
| glycerin-asparagine agar | G: good |
| | A: abundant, brownish gray(6E2) to black |
| | R: violet brown(11F8) |
| | S: trace of pale pink |
| peptone-yeast extract-iron agar | G: moderate |
| | A: none |
| | R: brown(6E4) |
| | S: pale brown |
| tyrosine agar | G: good |
| | A: abundant, brownish gray(9E2) to black |
| | R: dark violet(15F8) |
| | S: brown |
| sucrose-nitrate agar | G: moderate |
| | A: none |
| | R: yellowish white(4A2) |

TABLE 1-continued

| Cultural characteristics of the strain No. 89009 | |
|---|---|
| Medium | Cultural characteristics |
| S: | none |

Abbreviation: G = growth, A = aerial mycelium, R = reverse side color, S = soluble pigment The aerial mycelium was brownish gray. Part of colony became black and moist, and showed hygroscopic character on most agar media. Reverse side of growth was violet brown on yeast extract-malt extract agar and glycerin-asparagine agar, reddish brown on oatmeal agar. This mycelium pigment was pH sensitive, changing from red to dark violet with addition of 0.05N NaOH. Melanoid pigments were produced in ISP1 broth, peptone-yeast extract-iron agar and tyrosine agar. Trace of pale pink pigment was observed in oatmeal agar and glycerin asparagine agar. This soluble pigment was pH sensitive, changing from pink to violet with addition of 0.05N NaOH.

(iii) Cell Wall Type

The cell wall analysis was performed by the methods of Becker et al[4] and Yamaguchi[5].

Analysis of whole cell hydrolysates of strain No. 89009 showed the presence of LL-diaminopimelic acid. Accordingly, the cell wall of this strain is classified as type I.

(iv) Biological and Physiological Properties

Physiological properties and utilizatikon of carbon sources are shown in Tables 2 and 3, respectively.

Temperature range for growth was determined on yeast-malt extract agar using a temperature gradient incubator TN-3 (made by Advantec Toyo Co., Ltd.).

Utilization of carbon sources was examined according to the method of Pridham and Gottlieb[6].

TABLE 2

| Physiological properties of strain No. 89009 | |
|---|---|
| Conditions | Characteristics |
| temperature range for growth | 13° C.–42° C. |
| optimum temperature range for growth | 30° C.–35° C. |
| gelatin liquefaction | negative |
| milk coagulation | negative |
| milk peptonization | positive |
| starch hydrolysis | positive |
| production of melanoid pigments | positive |
| decomposition of cellulose | negative |
| production of $H_2S$ | negative |

TABLE 3

| Carbon utilization of the strain No. 89009 | |
|---|---|
| Compounds | Growth |
| D-glucose | + |
| sucrose | + |
| D-xylose | + |
| D-fructose | + |
| L-rhamnose | + |
| raffinose | ± |
| L-arabinose | + |
| inositol | + |
| mannitol | + |

+: utilization
±: doubtful utilization
−: no utilization

Based on the taxonomic properties described above, strain No. 89009 is considered to belong to the genus Streptomyces and to be a strain of the gray series of the Pridham and Tresner grouping[7]. Therefore, this strain was designated Streptomyces sp. No. 89009.

1) Shirling, E. B. and D. Gottlieb: Method for characterization of Streptomyces species. International Journal of Systematic Bacteriology, 16, 313–340, 1966

2) Waksman, S. A.: The actinomycetes Vol. 2: Classification, identification and description of genera and species: The Williams and Wilkins Co., Baltimore, 1961

3) Kornerup, A. and J. H. Wanscher: Methuen Handbook of Colour, Methuen, London, 1978

4) Becker, B., M. P. Lechevalier, R. E. Gordon and H. A. Lechevalier: Rapid differentiation between Nocardia and Streptomyces by paper chromatography of whole-cell hydrolysates: Appl. Microbiol. 12, 421–423, 1964

5) Yamaguchi, T.: Comparison of the cell wall composition of morphologically distinct actinomycetes: J. Bacteriol. 89, 444–453, 1965

6) Pridham, T. G. and D. Gottlieb: The utilization of carbon compounds by some Actinomycetales as an aid for species determination: J. Bacteriol. 56: 107–114, 1948

7) Buchanan, R. E. and N. E. Gibbons: Bergey's Manual of Determinative Bacteriology, 8th edition, pp. 748–829 (Pridham and Tresner): The Williams and Wilkins Co., Baltimore, 1974

(2) Production of FR901366 Substance and FR901367 Substance

FR901366 substance and FR901367 substance of this invention are produced when a strain which belongs to the genus Streptomyces (e.g. Streptomyces sp. No. 89009) and which is capable of producing FR901366 substance and/or FR901367 substance is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, starch, sucrose, fructose, glycerin, or the like.

The preferred sources of nitrogen are yeast extract, peptone, gluten meal, cotton seed flour, soybean meal, corn steep liquor, dried yeast, wheat germ, potato protein, or the like as well as inorganic and organic nitrogen compounds such as ammonium salts (e.g. ammonium nitrate, ammonium sulfate, ammonium phosphate, etc.), urea, amino acid, or the like.

The carbon and nitrogen sources, though advantageously employed in combination, need not to be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride sodium or potassium iodide, magnesium salts, copper salts, zinc salts, cobalt salts, or the like.

If necessary, especially when the culture medium foams seriously a defoaming agent, such as liquid paraffin, fatty oil, plant oil, mineral oil or silicone may be added.

As in the case of the preferred methods used for the production of other biologically active substances in massive amounts, submerged aerobic cultural conditions are preferred for the production of FR901366 substance and/or FR901367 substance in massive amounts.

For the production in small amounts, a shaking culture in a flask is employed.

Further, when the growth is carried out in large tanks, it is preferable to use the vegetative cells of the microorganism for inoculation in the production tanks in order to avoid growth lag in the process of production of FR901366 substance and/or FR901367 substance. Accordingly, it is desirable first to produce vegetative cells of the microorganism by inoculating a relatively small quantity of culture medium with cells of the microorganism and culturing said inoculated medium, and then to transfer the cultured vegetative cells to large tanks. The medium, in which the vegetative cells is produced, is substantially the same as or different from the medium utilized for the production of FR901366 substance and FR901367 substance.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 10° C. and 40° C., preferably 20° C. to 30° C., for a period of about 50 hours to 200 hours, which may be varied according to fermentation conditions and scales.

When the fermentation is completed, the culture broth is then subjected for the recovery of FR901366 substance and/or FR901367 substance to various processes conventionally used for recovery and purification of biological active substances, for instance, solvent extraction with an appropriate solvent or a mixture of some solvents, chromatography or recrystallization from an appropriate solvent or a mixture of some solvents.

According to this invention, in general, FR901366 substance and FR901367 substance are found in the filtered broth. Accordingly, it is preferable that the filtered broth is subjected to the isolation process of FR901366 substance and/or FR901367 substance, for example, by means of extraction using an appropriate solvent such as acetone, ethyl acetate or the like, a mixture of these solvents, or the like.

The extract is treated by a conventional manner to provide FR901366 substance and/or FR901367 substance, for example, the extract is concentrated by evaporation or distillation to a smaller amount and the resulting residue containing active material, i. e. FR901366 substance and/or FR901367 substance are purified by conventional purification processes, for example, chromatography or recrystallization from an appropriate solvent or a mixture of some solvents.

(3) Physico-chemical Properties of FR901366 Substance

FR901366 substance as obtained according to the fermentation process as mentioned above has the following physico-chemical properties.

Appearance:
white powders
Nature:
acidic substance
Melting point:
170°–172° C. (dec.)
Specific rotation:
$[\alpha]_D^{23}$ +92° (c=1.0, methanol)

Molecular formula:

$$C_{24}H_{25}NO_{10}S$$

Elemental Analysis: Calcd: for $C_{24}H_{25}NO_{10}S \cdot H_2O$: C, 53.63; H, 5.06; N, 2.61; S, 5.97 (%);
Found: C, 53.93; H, 5.28; N, 2.55; S, 4.50 (%).
Molecular weight:
519.54
FAB-MS m/z 520 $(M+H)^+$
HRFAB-MS m/z 520.1279 $[(C_{24}H_{24}NO_{10}S+H)$ requires 520.1277]
Solubility:
soluble; methanol, acetone
sparingly soluble: chloroform
insoluble; hexane, water
Color reaction:
positive: cerium sulfate reaction, sulfuric acid reaction, iodine vapor reaction
negative: ninhydrin reaction, Dragendorff reacgtion Thin layer chromatography (hereinafter referred to as TLC):

| Stationary phase | Developing solvent | Rf value |
|---|---|---|
| silica gel plate* | chloroform:methanol (5:1) | 0.0 |
| ODS** | methanol:water:trifluoroacetic acid (40:60:0.1) | 0.3 |
| | acetonitrile:water:trifluoroacetic acid (40:60:0.1) | 0.5 |

*silica gel plate, Kieselgel 60 $F_{254}$ (made by E. Merck)
**silica gel plate for reverse phase TLC, RP-18 $F_{254S}$ (made by E. Merck)
Ultraviolet absorption spectrum:
$\lambda_{max}^{methanol}$ nm(ε) 233(21000), 245(sh)(18000), 354(4600)
$\lambda_{max}^{methanol+HCl}$ nm 233, 245(sh), 354
$\lambda_{max}^{methanol+NaOH}$ nm 233, 410

Infrared absorption spectrum:
$\lambda_{max}^{KBr}$ 3400, 2920, 1700, 1640, 1530, 1430, 1360, 1340, 1300, 1250, 1220, 1160, 1090, 1080, 1000, 960 cm$^{-1}$ $^1$H Nuclear-magnetic resonance spectrum: (DMSO-$d_6$, 400 MHz) δ: 11.12 (1H, broad s), 8.12 (1H, d, J=8 Hz), 7.72 (1H, t, J=8 Hz), 7.62 (1H, broad s), 7.58 (1H, d, J=8 Hz), 7.34 (1H, d, J=8 Hz), 6.70 (1H, broad s), 5.80 (1H, broad s), 5.68 (1H, s), 4.06 (1H, m), 2.96 (1H, d, J=18 Hz), 2.54–2.38 (3H, m), 2.15 (1H, d, J=18 Hz), 2.12 (1H, m), 1.96 (3H, broad s)., 1.87 (1H, m), 1.74 (3H, s), 1.67 (1H, m).

$^{13}$C Nuclear magnetic resonance spectrum: (DMSO-$d_6$, 100 MHz) δ: 196.5 (s), 193.6 (s), 190.9 (s), 171.6 (s), 169.5 (s), 160.3 (s), 159.3 (s), 136.3 (d), 131.6 (s), 124.6 (d), 122.9 (d), 119.2 (d), 115.6 (s), 78.8 (s), 75.9 (s), 75.9 (s), 61.9 (s), 51.8 (d), 42.2 (t), 32.2 (t), 29.0 (t), 23.8 (q), 22.4 (q), 19.6 (t).

From above-mentioned physico-chemical properties, FR901366 substance is proved to have a following chemical formula:

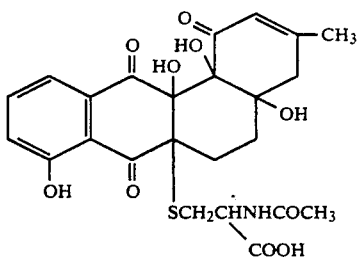

(4) Physico-Chemical Properties of FR901367 Substance:

FR901367 substance as obtained according to the fermentation process as mentioned above has the following physico-chemical properties.
Appearance:
Pale yellow powder
Nature:
acidic substance
Melting point:
156°–159° C. (dec.)
Specific rotation:
$[\alpha]_D^{23} + 148°$ (c=0.5, methanol)
Molecular formula:

$C_{24}H_{25}NO_{11}S$

Elemental Analysis: Calcd: for $C_{24}H_{25}NO_{11}S \cdot H_2O$:
C, 52.08; H, 4.92; N, 2.53; S, 5.79 (%);
Found: C, 52.16; H, 5.24; N, 2.76; S, 5.08 (%).
Molecular weight:
535.54
FAB-MS m/z 536 $(M+H)^+$
HRFAB-MS m/z 536.1223 [$(C_{24}H_{25}NO_{11}S+H)$ requires 536.1227]
Solubility:
soluble: methanol, ethanol
sparingly soluble: ethyl acetate, acetone, water
insoluble: n-hexane
Color reaction:
positive: iodine vapor reaction, cerium sulfate-sulfuric acid reaction,
negative: ninhydrin reaction, Molish reaction, Ehrlich reaction

| | TLC: | |
|---|---|---|
| Stationary phase | Developing solvent | Rf value |
| ODS* | acetonitrile:water:<br>trifluoroacetic acid<br>(20:80:0.1) | 0.52 |

*silica gel plate for reverse phase TLC, RP-18 WF$_{254}$S (made by E. Merck)
Ultraviolet absorption spectrum:
$\lambda_{max}^{methanol}$ nm 232, 248(sh), 354
Infrared absorption spectrum:
$\lambda_{max}^{KBr}$ 3400, 1720, 1660, 1640, 1520, 1450, 1420, 1370, 1340, 1250, 1220, 1160, 1110, 1070, 1040, 980, 930 cm$^{-1}$ $^1$H Nuclear magnetic resonance spectrum: (400 MHz, CD$_3$OD) δ: 7.70–7.67 (2H, m), 7.29 (1H, m), 5.84 (1H, m), 4.53 (1H, m), 4.36 (1H, dd, J=7 and 5 Hz), 2.95 (1H, broad d, J=18 Hz), 2.82 (1H, dd, J=13 and 7 Hz), 2.70–2.64 (2H, m), 2.25 (1H, d, J=18 Hz), 2.09 (1H, dd, J=15 and 3 Hz), 2.01 (3H, broad s), 1.84 (3H, s).

$^{13}$C Nuclear magnetic resonance spectrum: (100 MHz, DMSO-d$_6$) δ: 194.7 (s), 194.1 (s), 189.0 (s), 171.4 (s), 169.3 (s), 160.9 (s), 159.3 (s), 136.5 (d), 131.5 (s), 124.3 (d), 123.0 (d), 119.3 (d), 115.0 (s), 79.3 (s), 76.9 (s), 75.9 (s), 67.9 (d), 61.9 (s), 51.5 (d), 43.2 (t), 35.2 (t), 32.7 (t), 23.7 (q), 22.3 (q).

From above-mentioned physico-chemical properties, FR901367 substance is proved to have a following chemical formula

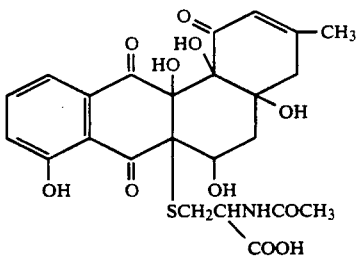

(5) Production of FR131132 Substance and FR134851 Substance

The compounds in which $R^1$ is hydrogen, $R^2$ is hydrogen, $R^3$ is carboxy, $R^4$ is hydrogen, $R^5$ is hydrogen, $R^6$ is hydrogen and $R^7$ is hydrogen (hereinafter referred to as FR131132 substance), and a compound in which $R^1$ is hydoxy, $R^2$ is hydrogen, $R^3$ is carboxy, $R^4$ is hydrogen, $R^5$ is hydrogen, $R^6$ is hydrogen and $R^7$ is hydrogen (hereinafter referred to as FR134851 substance) are prepared by a hydrolysis of FR901366 substance and FR901367 substance using a bacterium belonging to the genus Pseudomonas such as Pseudomonas cepacia No. 97 which is capable to hydrolyse FR901366 substance and FR901367 substance.

Particulars of the microorganism used in this process are explained in the following.

Taxonomic studies on the strain No. 97

The strain No. 97 was isolated from a soil sample obtained from Ibaraki-ken, JAPAN.

The methods described in Bergey's Manual of Systematic Bacteriology (Volume 1) were employed principally for this taxonomic study.

(i) Morphological Characteristics

Morphological observation of the strain No. 97 was carried out by the optical and electron microscopes with cells cultured on nutrient broth and agar at 30° C. for 20 hours.

The strain No. 97 was a gram-negative, motile bacterium. The cell shapes were rod and about 1.0–1.2×1..5–3.0 μm is in size.

Results were shown in Table 4.

TABLE 4

| Morphological characteristics of the stain No. 97 | |
|---|---|
| Gram stain | negative |
| color of colony | grayish yellow<br>(on nutrient agar) |
| cell shape | rod |
| cell size | 1.0–1.2 × 1.5–3.0 μm |
| spore | negative |
| motility | positive |

Physiological characteristics of the strain No. 97 were summarized in Table 5. The growth temperature range was from 8° C. to 34° C.

The strain No. 97 was oxidase positive, catalase positive and O-F test oxidative. This strain hydrolyzed gelatin and casein. Starch hydrolysis was negative. Lysin decarboxylase, ornitine decarboxylase were positive. Arginine dihydrolase was negative. Acid formation was observed from D-glucose, D-mannitol, D-fructose, D-xylose, lactose, maltose and sucrose.

TABLE 5

Physiological characteristics of the strain No. 97

| Conditions | Characteristics |
|---|---|
| growth temperature | 8–34° C. |
| growth in air | positive |
| growth on MacConkey agar | positive |
| catalase | positive |
| oxidase | positive |
| O—F test | oxidative |
| $H_2S$ (SIM) | negative |
| Simons citrate | positive |
| indole | negative |
| nitrate reaction | positive |
| gelatin liquefaction | positive |
| casein hydrolysis | positive |
| esculin hydrolysis | negative |
| starch hydrolysis | negative |
| ONPG test | positive |
| DNase | negative |
| Tween 80 hydrolysis | positive |
| lysin decarboxylase | positive |
| arginine dihydrolase | negative |
| ornithine decarboxylase | positive |
| acid from sugar | |
| D-glucose | positive |
| D-mannitol | positive |
| D-fructose | positive |
| D-xylose | positive |
| lactose | positive |
| maltose | positive |
| sucrose | positive |
| salicin | negative |

(iii) Identification

According to Bergey's Manual of Systematic Bacteriology (Volume 1), the strain No. 97 was considered to belong to the genus Pseudomonas sp. from those characteristics described above.

After comparing the described in Bergey's Manual of Systematic Bacteriology (Volume 1), *Pseudomonas cepacia* Palleroni and Holmes 1981 was selected for further detail comparison.

Therefore, the strain No. 97 was compared with *Pseudomonas cepacia*. No significant difference was observed between the two cultures and the properties of the strain No. 97 showed good agreement with *Pseudomonas cepacia*.

The strain No. 97, therefore, was identified as *Pseudomonas cepacia*.

A culture of *Pseudomonas cepacia* No. 97 has been deposited with Fermentation Research Institute Agency of Industrial Science and Technology (1-3, Higashi 1 chome Tsukuba-shi, IBARAKI, 305 JAPAN) on June 6, 1990 under the number of FERM BP-2945.

Physico-Chemical Properties of FR131132 Substance

FR131132 substance obtained according to the deacetylation process as mentioned above has the following physico-chemical properties.
  Appearance:
  white powders
  Nature:
  amphoteric substance
  Melting point:
  220°–225° C. (dec.)
  Specific rotation:
  $[\alpha]_D^{23} + 115°$ (c = 1.0, dimethylsulfoxide)
  Molecular formula:

$C_{22}H_{23}NO_9S$

Elemental Analysis: Calcd: for $C_{22}H_{22}H_{23}NO_9S \cdot H_2O$: C, 53.33; H, 5.09; N, 2.83; S, 6.47 (%);
  Found: C, 52.76; H, 5.07; N, 2.69; S, 6.89 (%).
  Molecular weight:
  477.50
  FAB-MS m/z: 478 $(M+H)^+$
  HRFAB-MS: m/z: 478.1176 $[(C_{22}H_{23}NO_9S+H)$ requires 478.1172]
  Solubility:
  sparingly soluble: water, methanol, ethanol insoluble: chloroform, n-hexane
  Color reaction:
  positive: cerium sulfate reaction, sulfuric acid reaction, iodine vapor reaction
  negative: Dragendorff reaction, potassium permanganate reaction Ultraviolet absorption spectrum:
$\lambda_{max}^{methanol}$ nm($\epsilon$) 233(22000), 245(sh)(19000), 354(5000)
$\lambda_{max}^{methanol+HCl}$ nm 233, 245(sh), 354
$\lambda_{max}^{methanol+NaOH}$ nm 233, 410
Infrared absorption spectrum:
$\nu_{max}^{KBr}$ 3600, 3350, 3200, 1700, 1650, 1630, 1575, 1450, 1420, 1380, 1340, 1300, 1220, 1160, 1100, 1070, 1040, 1000, 980, 960, 935 cm$^{-1}$ $^1H$ Nuclear magnetic resonance spectrum: a(DCl-$D_2O$, 400 MHz) δ: 7.58–7.48 (2H, m), 7.18 (1H, dd, J = 8 and 1 Hz), 5.74 (1H, broad s), 3.89 (1H, m), 2.80 (1H, broad d, J = 18 Hz), 2.68 (1H, dd, J = 14 and 6 Hz), 2.52 (1H, dd, J = 14 and 5 Hz), 2.31 (1H, m), 2.17 (1H, d, J = 18 Hz), 2.02 (1H, m), 1.83 (3H, s), 1.79 (1H, m), 1.61 (1H, m).

$^{13}C$ Nuclear magnetic resonance spectrum: (DCl-$D_2O$, 100 MHz) δ: 198.7 (s), 198.6 (s), 194.0 (s), 171.7 (s), 167.5 (s), 162.4 (s), 139.8 (d), 133.2 (s), 128.0 (d), 124.8 (d), 123.1 (d), 117.1 (s), 81.4 (s), 78.9 (s), 78.9 (s), 64.3 (s), 54.5 (d), 44.6 (t), 32.5 (t), 31.0 (t), 26.1 (q), 21.4 (t).

From above-mentioned physico-chemical properties, FR131132 substance is proved to have a following chemical formula:

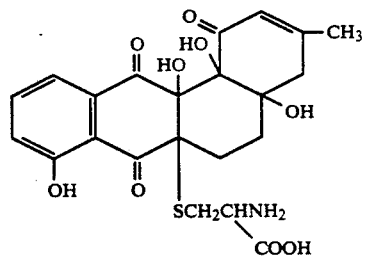

Physico-Chemical Properties of FR134851 Substance

FR134851 substance obtained according to the deacetylation process as mentioned above has the following physico-chemical properties.
  Appearance:
  white powders
  Nature:
  amphoteric substance
  Molecular weight:

$C_{22}H_{23}NO_{10}S$

Molecular weight:
493.50
FAB-MS: m/z: 494 (M+H)+
Solubility:
soluble: methanol, ethanol
sparingly soluble: water
insoluble: chloroform, n-hexane
Color reaction:
positive: cerium sulfate reaction, sulfuric acid reaction, iodine vapor reaction, Ninhydrin reaction
negative: Dragendorff reaction, potassium permanganate reaction Ultraviolet absorption spectrum:
$\lambda_{max}^{methanol}$ nm($\epsilon$) 233(22000), 245(sh)(19000), 354(5000)
$\lambda_{max}^{methanol+HCl}$ nm 233, 245(sh), 354
$\lambda_{max}^{methanol+NaOH}$ nm 233, 410

$^1$H Nuclear magnetic resonance spectrum: (CD$_3$OD, 400 MHz) δ: 7.72–7.67 (2H, m), 7.31 (1H, m), 5.86 (1H, m), 4.60 (1H, t, J=3 Hz), 3.45 (1H, dd, J=8 and 4 Hz), 2.96 (1H, broad d, J=18 Hz), 2.83 (1H, dd, J=13 and 8 Hz), 2.77 (1H, dd, J=13 and 4 Hz), 2.70 (1H, dd, J=15 and 3 Hz), 2.27 (1H, d, J=18 Hz), 2.08 (1H, dd J=15 and 3 Hz), 2.01 (3H, s).

From above-mentioned physico-chemical properties, FR134851 substance is proved to have a following chemical formula:

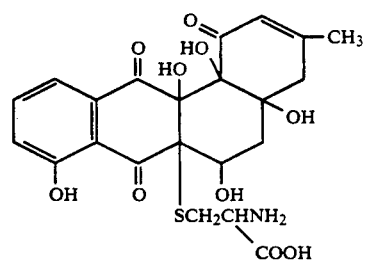

(6) Production of Other Compounds

Other compounds can be prepared by synthetic methods in the following processes.

Process 1

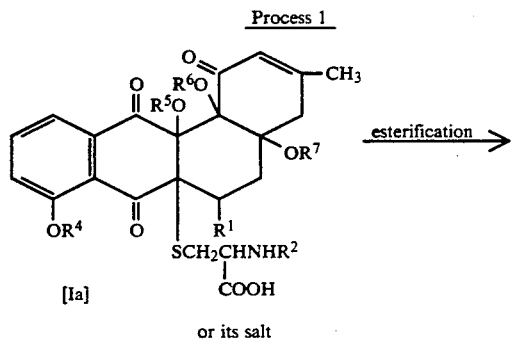

[Ia] or its salt

→ esterification

Process 1

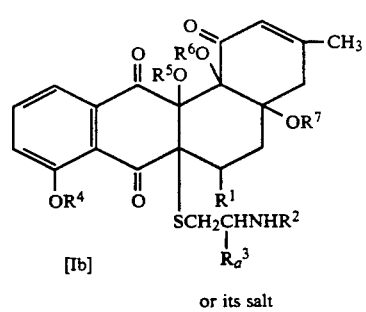

[Ib] or its salt

Process 2

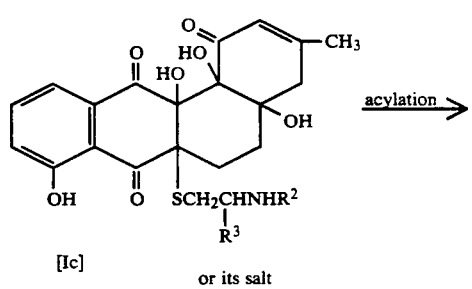

[Ic]

→ acylation

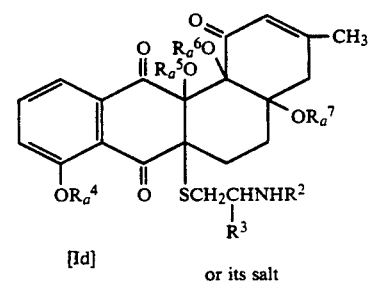

[Id] or its salt

Process 3

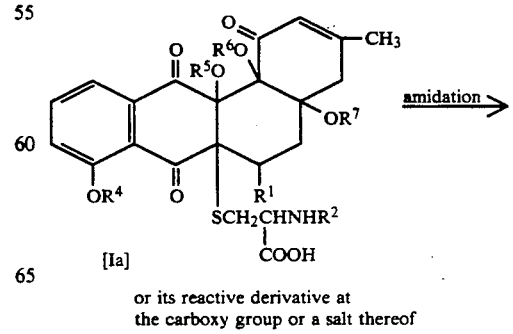

[Ia] or its reactive derivative at the carboxy group or a salt thereof

→ amidation

-continued
Process 3

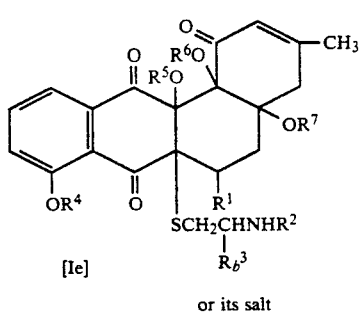

[Ie]

or its salt

Process 4

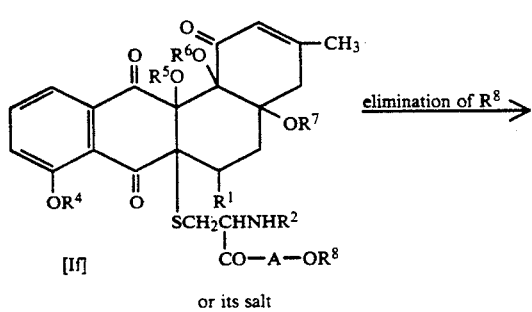

[If]

or its salt

→ elimination of R⁸ →

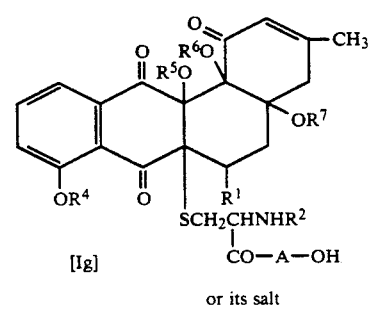

[Ig]

or its salt

Process 5

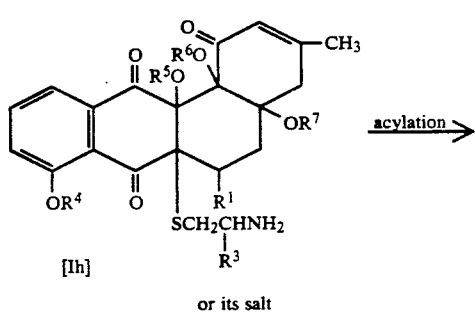

[Ih]

or its salt

-continued
Process 5

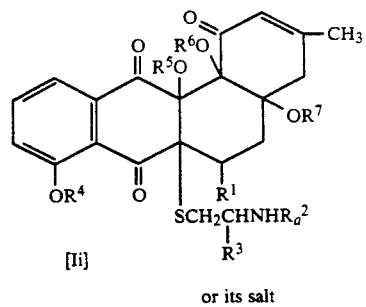

[Ii]

or its salt

Process 6

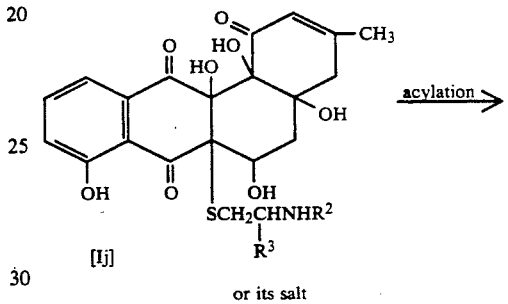

[Ij]

or its salt

→ acylation →

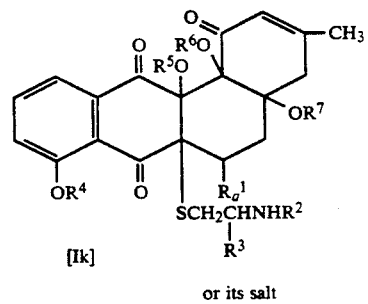

[Ik]

or its salt wherein $R^1$, $R^2$, $R^3$, $R^4$, $R^5$ and $R^6$ are each as defined above, $R_a^3$ is esterified carboxy, at least one of $R_a^4$, $R_a^5$, $R_a^6$ and $R_a^7$ is acyl and the other is(are) hydrogen or acyl, $R_a^1$ is acyloxy, $R_b^3$ is carbamoyl, lower alkyl-carbamoyl which may be substituted with hydroxy, or a group of the formula: —CO—A—OR⁹, in which A is amino acid(s) residue, and $R^9$ is hydrogen or a carboxy protective group, $R^8$ is a carboxy protective group, and $R_a^2$ is acyl.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" may be a straight or branched one such as methyl, ethyl, propyl, isopropyl, butyl, isobutyl, tert-butyl, pentyl, hexyl or the like.

Suitable "acyl" and acyl moiety in the term "acyloxy" may be carboxy, esterified carboxy, carbamoyl, lower alkyl-carbamoyl, alkanoyl, ar(lower)alkanoyl, aroyl, a group of the formula: —CO—A—OR$^9$, wherein A and R$^9$ are each as defined above, and the like.

The esterified carboxy may be substituted or unsubstituted lower alkoxycarbonyl (e.g. methoxycarbonyl, ethoxycarbonyl, propoxycarbonyl, butoxycarbonyl, tert-butoxycarbonyl, hexyloxycarbonyl, 2-iodoethoxycarbonyl, 2,2,2-trichloroethoxycarbonyl, etc.), substituted or unsubstituted aryloxycarbonyl (e.g. phenoxycarbonyl, 4-nitrophenoxycarbonyl, 2-naphthyloxycarbonyl, etc.), substituted or unsubstituted ar(lower)alkoxycarbonyl (e.g. benzyloxycarbonyl, phenethyloxycarbonyl, benzhydryloxycarbonyl, 4-nitrobenzyloxycarbonyl, etc.) and the like.

The lower alkyl-carbamoyl may be methylcarbamoyl, ethylcarbamoyl, propylcarbamoyl, dimethylcarbamoyl, diethylcarbamoyl and the like, which may be substituted with hydroxy, in which preferable one is hydroxyethylcarbamoyl.

The alkanoyl may be formyl, acetyl, propionyl, butyryl, isobutyryl, valeryl, isovaleryl, pivaloyl, hexanoyl and the like.

The ar(lower)alkanoyl may be substituted or unsubstituted one such as phenylacetyl, phenylpropionyl, naphthylacetyl, tolylacetyl, chlorophenylacetyl, and the like, in which preferable one is chlorophenylacetyl.

The aroyl may be benzoyl, naphthoyl, toluoyl, xyloyl, and the like, in which preferable one is benzoyl.

Suitable "amino acid(s) residue" means a bivalent residue derived from amino acid(s), and such amino acid may be neutral amino acid such as glycine, D- or L-alanine, β-alanine, D-or L-valine, D-or L-leucine, D- or L-isoleucine, D-or L-serine, D- or L-threonine, D- or L-cysteine, D- or L-methionine, D- or L-phenylalanine, D- or L-tryptophan, D- or L-tyrosine, D- or L-proline, D- or L-4-hydroxyproline, D- or L-pyroglutamic acid, acidic amino acid such as D- or L-glutamic acid, D- or L-aspartic acid, D- or L-β-aspartic acid, D- or L-glutamine, D- or L-asparagine, and basic amino acid such as D- or L-lysine, D- or L-arginine, D- or L-histidine, D- or L-ornithine, and combination of two of such amino acid, in which preferable one is isoleucine or combination of isoleucine and tryptophan.

Suitable "carboxy protective group" may include a conventional protective group, which is used in the field of amino acid and peptide chemistry, that may be lower alkyl as mentioned above, aryl (e.g. phenyl, tolyl, naphthyl, etc.), ar(lower)alkyl (e.g. benzyl, phenethyl, etc.), and the like, in which preferable one is methyl.

Pharmaceutically acceptable salts of ANTHRAQUINONE DERIVATIVES can be prepared by a conventional method, e.g. by treating them with a base or an acid.

The suitable base may be an alkali metal (e.g. sodium, potassium, etc.,), an alkaline earth metal (e.g. magnesium, calcium, etc.), the hydroxide or carbonate thereof, alkali metal alkoxide (e.g. sodium methoxide, sodium ethoxide, potassium tert-butoxide, etc.), ammonia, an organic base (e. g. trimethylamine, triethylamine, etc.) and the like.

The suitable acid may be an inorganic acid (e.g. hydrochloric acid, hydrobromic acid, sulfuric acid, phosphoric acid, etc.), an organic acid (e.g. formic acid, acetic acid, trifluoroacetic acid, maleaic acid, tartaric acid, methanesulfonic acid, benzensulfonic acid, toluenesulfonic acid, etc.) and the like.

Pharmaceutically acceptable salts of ANTHRAQUINONE DERIVATIVES are conventional non-toxic salts and include the salts with said base or an acid. The salts of ANTHRAQUINONE DERIVATIVES is also included within the scope of this invention.

With respect to the ANTHRAQUINONE DERIVATIVES [I] of this invention, it is to be understood that there may be optical isomers due to asymmetric carbon atom(s), and such isomers are also included within the scope of this invention.

The processes for preparing the object compounds [I] of the present invention are explained in detail in the following.

PROCESS 1

The compound [Ib] or its salt can be prepared by subjecting a compound [Ia] or its salt to esterification reaction.

Suitable salts of the compounds [Ia] and [Ib] may be the same as those exemplified for the compound [I].

Suitable esterifing agent to be used in this reaction may be a conventional one such as an alcohol (e.g. methanol, ethanol, propanol, isopropanol, etc.) or its reactive equivalent (e.g. halide, sulfonate, sulfate, diazo compound, tri(alkyl)silyldiazo compound, etc.), and the like.

The reaction is preferably conducted in the presence of an organic or inorganic base such as alkali metal (e.g. lithium, sodium, potassium, etc.), alkaline earth metal (e. g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-N,N,-dimethylaminopyridine, etc.), quinoline, and the like.

In case that the esterifing agent is the alcohol in this reaction, it is preferable to carry out the reaction, in the presence of a conventional condensing agent such as N,N-dicyclohexylcarbodiimide, N-etyl-N'-(3-dimethylaminopropyl)carbodiimide, N,N'-carbonyl-bis-(2-methylimidazole), ethyl polyphosphate, isopropyl polyphosphate, phosphorus oxychloride (phosphoryl chloride), phosphorus trichloride, diphenyl phosphorylazide, thionyl chloride, oxalyl chloride, lower alkyl haloformate (e.g. ethyl chloroformate, isopropyl chloroformate, etc.), triphenylphosphine, 1-(p-chlorobenzenesulfonyloxy)-6-chloro-1H-benzotriazole, so-called Vilsmeier reagent prepared by the reaction of N,N-dimetylformamide with thionyl chloride, phosgene, trichloromethyl chloroformate, phosphorus oxychloride, oxalyl chloride, etc., or the like.

The reaction is usually carried out in a conventional solvent which does not adversely influence the reaction such as an alcohol (e.g. methanol, ethanol, etc.) diethyl ether, dioxane, chloroform, dichloromethane, tetrahydrofuran, N,N-dimethylformamide, etc., and further in case that the base or the esterifing agent is in liquid, it can be used as a solvent.

The reaction temperature is not critical and the reaction can be carried out under cooling, at ambient temperature, or under heating.

PROCESS 2

The compound [Id] or its salt can be prepared by reacting a compound [Ic] or its salt with an acylating agent.

Suitable salts of the compounds [Ic] and [Id] may be the same as those exemplified for the compound [I].

The acylating agent may include an organic acid represented by the formula: $R^{10}$-OH, in which $R^{10}$ is acyl as illustrated above, or its reaction derivative.

As suitable reaction derivative of organic acid, there may be a conventional one such as an acid halide, an acid anhydride, an activated amide, an activated ester or the like.

Suitable examples are acid halides such as acid chloride and acid bromide, mixed acid anhydrides with various acids (e.g. substituted phosphoric acid such as dialkyl phosphoric acid, sulfuric acid, aliphatic carboxylic acid, aromatic carboxylic acid, etc.), symmetric acid anhydrides, active amides with various imidazoles, and active esters such as cyanomethyl ester, methoxymethyl ester, p-nitrophenyl ester, 2,4-dinitrophenyl ester, pentachlorophenyl ester, phenylazophenyl ester, carboxymethylthio ester and 1-hydroxy-1H-benzatriazole ester, N-hydroxysuccinimide ester. The kind of such reactive derivatives can be selected depending on the kind of acyl group to be introduced.

When free acid is used as an acylating agent, the acylation reaction may preferably be conducted in the presence of a conventional condensing agent as illustrated in Process 1.

The reaction is also preferably carried out in the presence of a conventional base such as triethylamine, pyridine, sodium hydroxide or the like.

The reaction is usually carried out in a conventional solvent such as water, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof, and further in case that the base or the acylating agent is in liquid, it can be used as a solvent.

The reaction temperature is not critical and the reaction can be carried out under cooling to heating.

In the present reaction, when the compound [Ic] having hydrogen for $R^2$ as a starting compound is used, the compound [Id] having acyl for $R^2$ may be obtained according to reaction conditions. This case is also included within the scope of the present reaction.

PROCESS 3

The compound [Ie] or its salt can be prepared by reacting a compound [Ia] or its reactive derivative at the carboxy group or a salt thereof with ammonia, lower alkylamine, or amino acid(s).

Suitable salts of the compounds [Ie] and [Ia] and its reactive derivative may be the same as those exemplified for the compound [I].

Suitable "lower alkylamine may be mono or di(-lower)alkylamine such as metylamine, ethylamine, propylamine, dimethylamine, diethylamine or the like, which may be substituted with hydroxy.

Suitable "amino acid(s)" can be referred to the ones as exemplified for amino acid(s) residue, which may have protected carboxy.

Suitable reactive derivative at the carboxy group can be referred to ones as exemplified for reactive derivative of organic acid in Process 2.

The reaction is usually carried out in a conventional solvent such as water, acetone, dioxane, chloroform, methylene chloride, ethylene chloride, tetrahydrofuran, ethyl acetate, N,N-demethylformamide, pyridine or any other organic solvent which does not adversely influence the reaction. Among these solvents, hydrophilic solvents may be used in a mixture with water.

When the compound [Ia] is used in a free acid form in the reaction, the reaction is preferably carried out in the presence of a conventional condensing agent as illustrated in Process 1.

The reaction temperature is not critical, and the reaction can be carried out under cooling to heating.

PROCESS 4

The compound [Ig] or its salt can be prepared by subjecting a compound [If] or its salt to elimination reaction of $R^8$.

Suitable salts of the compounds [If] and [Ig] may be the same as those exemplified for the compound [I].

The reaction is carried out in accordance with a conventional method such as hydrolysis, reaction or the like.

The hydrolysis is preferably carried out in the presence of a base or an acid including Lewis acid.

Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]non-5-ene, 1,4-diazobicyclo[2,2,2,]octane, 1,8-diazabicyclo[5,4,-0]undec-7-ene, or the like.

Suitable acid may include an organic acid (e.g. formic acid, acetic acid, propionic acid, trichloroacetic acid, trifluoroacetic acid, etc.), an inorganic acid (e.g. hydrochloric acid, hydrobromic acid, hydroiodic acid, sulfuric acid, etc.) and Lewis acid (e.g. boron tribromide, etc.).

The reaction is usually carried out in a solvent such as water, an alcohol (e.g. methanol, ethanol, etc.), methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction can be applied preferably for elimination of the ester moiety such as 4-nitrobenzyl, 2-iodoethyl, 2,2,2,-trichloroethyl, or the like. The reduction method applicable for the elimination reaction may include chemical reduction and catalytic reduction.

Suitable reducing agents to be used in chemical reduction are a combination of metal (e.g. tin, zinc, iron, etc.) or metallic compound (e.g. chromium chloride, chromiun acetate, etc.) and an organic or inorganic acid (e. g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalyst (e.g. platinum plate, spongy platinum, platinum black, colloidal platinum, platinum oxide, platinum wire, etc.), palladium catalyst (e.g. spongy palladium, palladium black, palladium oxide, palladium on carbon, colloidal palladium, palladium on barium sulfate, palladium on barium carbonate, etc.), nickel catalyst (e.g. reduced nickel, nickel oxide, Raney nickel, etc.), cobalt catalyst (e.g.

reduced cobalt, Raney cobalt, etc.), iron catalyst (e.g. reduced iron, Raney iron, etc), copper catalyst (e.g. reduced copper, Raney copper, Ullman copper, etc.) or the like.

The reduction is usually carried out in a conventional solvent which does not adversely influence the reaction such as water, an alcohol (e.g. methanol, ethanol, propanol, etc.), N,N-diemthylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

In the present reaction, when the compound [If] having acyloxy for $R^1$, acyl for $R^4$, acyl for $R^5$, acyl for $R^6$ and/or acyl for $R^7$ is used as a starting compound, the compound [Ig] having hydroxy for $R^1$, hydrogen for $R^4$, hydrogen for $R^5$, hydrogen for $R^6$ and/or hydrogen for $R^7$ may be obtained according to reaction conditions. This case is also included within the scope of the present reaction.

PROCESS 5

The compound [Ii] or its salt can be prepared by reacting a compound [Ih] or its salt with an acylating agent.

Suitable salt of the compound [Ih] may be the same as those exemplified for the compound [I].

Suitable salt of the compound [Ii] can be referred to the salt with the base as exemplified for the compound [I].

This reaction can be carried out in substantially the same manner as that of Process 2, and therefore the reaction mode and reaction conditions (e.g. solvent, reaction temperature, etc.) of this reaction are to be referred to those as explained in Process 2.

PROCESS 6

The compound [Ik] or its salt can be prepared by reacting a compound [Ij] or its salt with an acylating agent.

Suitable salts of the compound [Ik] and [Ij] may be the same as those exemplified for the compound [I].

This reaction can be carried out in substantially the same manner as that of Process 2, and therefore the reaction mode and reaction condition (e.g. solvent, reaction temperature, etc.) of this reaction are to be referred to those as explained in Process 2.

In the present reaction, when the compound [Ij] having hydrogen for $R^2$ as a starting compound is used, the compound [Ik] having acyl for $R^2$ may be obtained according to reaction conditions.

This case is also include within the scope of the present reaction.

(7) Biological Properties of ANTHRAQUINONE DERIVATIVES

For showing endothelin antagonistic activity of ANTHRAQUINONE DERIVATIVES, some test data are explained in the following.

TEST 1

Radioligand Binding Assay (a) Preparation of crude receptor membrane fractions

Porcine aorta was purchased from Pel-Freez Biologicals (U.S.A.) and stored at $-80°$ C. until use.

Porcine aorta (50 g) was thawed and dissected free from fatty tissue, minced with scissors and then homogenized with a polytron (Brinkmann PT-20, maximal speed for $3 \times 10$ sec) in 100 ml buffer (0.25 M sucrose, 10 mM Tris-HCl, 0.1 mM EDTA, pH 7.5).

The homogenate was centrifuged at 10,000 g for 20 minutes at 4° C.

The supernatant, containing the plasma membrane fraction, was centrifuged at 100,000 g for 60 minutes at 4° C., and then resultant pellets were referred to as crude membrane fractions.

The pellets were resuspended in 25 ml of binding assay buffer (50 mM Tris-HCl, 100 mM NaCl, 5 mM $MgCl_2$, 1.5 μg/ml phenylmethylsulfonyl fluoride (PMSF), 120 μg/ml bacitracin, 12 μg/ml leupepcin, 6 μg/ml chymostain, 0.1% bovine serum albumin (BSA), pH 7.5)

The aorta membrane fractions were stored at $-80°$ C. until use.

(b) $^{125}$I-Endothelin Binding Assay $^{125}$I-Endothelin ($1.67 \times 10^{-11}$ M) (Amersham Japan, specific activity: 2000 Ci/m mol) was incubated with 50 μl of the aorta membrane fractions in binding assay buffer at room temperature (20°-22° C.) for 60 minutes in a final volume of 250 μl.

After incubation, the incubation mixture were filtered through Glass-fiber GF/C filter (pretreated with 0.1% polyethylene imine for 3 hours prior to use) using cell harvester (Brandel M-245). The filters were then washed ten times with a total of 3 ml of the washing buffer (50 mM Tris-HCl, pH 7.5) at 0° C. The filters were counted in a gamma counter (Packard Auto Gamma Model 5650).

FR901367 substance competes with $^{125}$I-endothelin for binding to porcine aorta membrane fractions.

The activity of test compounds was expressed as $IC_{50}$ value, i.e. concentration required to compete with $^{125}$I-endothelin for binding to prorcine aorta membrane fractions by 50%.

The results are shown in Table 6.

TABLE 6

| Test Compounds | $IC_{50}$ value (μg/ml) |
| --- | --- |
| FR901366 described in Example 1 | 3.1 |
| FR901367 described in Example 2 | 0.36 |
| FR131132 described in Example 3 | 70 |
| FR134851 described in Example 4 | 10.2 |
| FR134624 described in Example 5 | 5.6 |
| FR134625 described in Example 6 | 250 |
| FR129795 described in Example 7 | 1.5 |
| FR129796 described in Example 8 | 8.0 |
| FR129797 described in Example 8 | 6.5 |
| FR134762 described in Example 9 | 8.6 |
| FR134763 described in Example 10 | 31 |
| FR134764 described in Example 11 | 9.8 |
| FR134761 described in Example 12 | 5.8 |
| FR131668 described in Example 13 | 9.8 |
| FR131661 described in Example 14 | 12.8 |
| FR131662 described in Example 15 | 2.5 |
| FR131663 described in Example 16 | 24.4 |
| FR131667 described in Example 17 | 58.0 |

TEST 2

Effect of FR901366 Substance and FR901367 Substance on Rabbit Aorta of Contraction Response of Endothelin Thoracic aorta were isolated from freshly killed male albino rabbits (11 weeks old) and cut into 25 mm strips with the intima denuded. After removing fatty tissues, these arterial segments (2 mm width and 25 mm length) were suspended in 25 ml organ chambers filled with Krebs-Ringer solution (113 mM NaCl, 4.8 mM KCl, 2.2 mM $CaCl_2$, 1.2 mM $MgCl_2$, 25 mM $NaHCO_3$, 1.2 mM $KH_2PO_4$, 5.5 mM glucose) maintained at 37° C. and gassed with 95% $O_2$/5% $CO_2$.

A preload of 1 g was applied after the aorta had been conditioned by application of increasing concentration of KCl. Contractions were measured as an increase in isometric tension.

The test compound was tested against contraction response of endothelin ($3.2 \times 10^{-9}$ M). Synthetic endothelin was obtained from Peptide Institute Inc. (Osaka, Japan). The test compound substance was added after the full contraction response induced endothelin.

The activity of the test compounds is expressed as the percentage inhibition of maximum contraction response induced by endothelin and shown in Table 7.

TABLE 7

Inhibition of against contraction response of rabbit thoracic aorta induced by endothelin

| Test compound | Inhibition (%) Concentration (M) | |
| --- | --- | --- |
|  | $1 \times 10^{-5}$ | $1 \times 10^{-4}$ |
| FR901366 substance in Example 1 | 15 | 39 |
| FR901367 substance in Example 2 | 38.6 | 75.0 |
|  |  | n = 3 |

TEST 3

Assay of In Vivo Pressor Effect in Conscious Rats

Male Wister rats (10 weeks old) were used. The mean arterial blood pressure was recorded from femoral artery via polyethylene catheter connected to the pressure transducer which was coupled to a Biophysiograph 180 system (Nihondenki-San-Ei Instrument Co., Ltd.).

FR901366 substance and endothelin were dissolved in saline and injected in bolus (0.2 ml) through polyethylene cateter inserted via femoral vein.

FR901366 substance was administered 3 minutes before the injection of endothelin. Inhibitory activity of FR90136 substance (10 mg/kg, i. v.) against endothelin (2.4 μg/kg, i. v.) induced pressor response was evaluated with a group of three rats and shown in Table 8.

TABLE 8

Inhibition of endothelin induced pressor response by venous injection of FR901366 substance

| Drug | Inhibition of endothelin pressor response (%) Time after administration | | | | | |
| --- | --- | --- | --- | --- | --- | --- |
|  | 5 | 10 | 20 | 30 | 60 | 120 (min) |
| FR901366 substance (10 mg/kg) | 27.2 | 50.0 | 63.3 | 53.8 | 66.6 | 50.0 |

From the test results, it is realized that ANTHRAQUINONE DERIVATIVES have a biological activity.

From the results of the above-mentioned biological test, ANTHRAQUINONE DERIVATIVES have endothelin antagonistic activity, therefore can be used as vasodilator for the treatment of hypertension such as peripheral circulatory failure, heart disease such as angina pectoris, cardiomyopathy, arteriosclerosis, myocardial infarction or the like, Raynaud's disease, cerebral stroke such as cerebral arterial spasm, cerebral ischemia, late phase cerebral spasm after subarachnoid hemorrhage or the like, asthma such as bronochoconstriction of the like, renal failure such as acute renal failure, or the like.

(8) Pharmaceutical Compositions

The pharmaceutical composition on this invention can be used in the form of a pharmaceutical preparation, for example, in solid, semisolid or liquid form, which contains ANTHRAQUINONE DERIVATIVES, as an active ingredient in admixture with an organic or inorganic carrier or excipient suitable for external, oral or parentetal applications. The active ingredient may be compounded, for example with the usual non-toxic, pharmaceutically acceptable carriers for tablets, pellets, capsultes, suppositories, solutions, emulsions, suspensions, and any other form suitable for use. And, if necessary, in addition, auxiliary, stabilizing, thickening and coloring agents and perfumes may be used. ANTHRAQUINONE DERIVATIVES may be included in the pharmaceutical composition in an amount sufficient to produce the desired effect upon the process or condition of diseases.

For applying the composition to human, it is preferable to apply it be intravenous, intramuscular or oral administration. While the dosage of therapeutically effective amount of ANTHRAQUINONE DERIVATIVES varies from and also depends upon the age and condition of each individual patient to be treated, in the case of intravenous administration, a daily dose of 0.1-100 mg of ANTHRAQUINONE DERIVATIVES per kg weight of human being, in the case of intramuscular administration, a daily dose of 0.1-100 mg of ANTHRAQUINONE DERIVATIVES per kg weight of human being, in case of oral administration, a daily dose of 1.0-100 mg of ANTHRAQUINONE DERIVATIVES per kg weight of human being is generally given as vasodilator for the treatment of above-mentioned diseases.

(9) EXAMPLES

The following examples are given for the purpose of illustrating the present invention in more detail.

EXAMPLE 1

(i) Fermentation

A aqueous seed medium (160 ml) containing soluble starch (1%), sucrose (1%), glucose (1%), cotton seed flour (1%), peptone (0.5%), soybean meal (0.5%) and calcium carbonate (0.2%) (pH was adjusted to 7.0 with 6N NaOH) was poured into each of twenty 500 ml-Erlenmeyer flasks and sterilized at 120° C. for 30 minutes.

A loopful of slant culture of Streptomyces sp. No. 89009 (FERM BP-2474) was inoculated to each of the media and cultured at 30° C. for 3 days on a rotary shaker (220 rpm, 5.1 cm throw). The resultant seed culture was inoculated to 160 liters of sterile fermentation medium consisting of starch (4%), peanut powder (1%), dried yeast (0.2%), wheat germ (0.5%), potato protein (0.5%) and calcium carbonate (0.2%) in a 200-liter stainless steel jar fermentor.

The fermentation was carried out at 25° C. for 7 days under aeration of 160 liters/minute and agitation of 200 rpm. An amount of FR901366 substance in the fermentation broth was quantified by high performance liquid chromatography (HPLC) using Hitachi Model 655 pump. A steel column (4.0 mm inside diameter, 250 mm length) packed with LiChrosphere RP-18 (made by E. Merck) was used at a flow rate of 1.0 ml/minute.

Mobile phase used was a mixture of acetonitrile and water (3:7) with 0.1% trifluoroacetic acid.

The sample for the HPLC assay was prepared as follows:

Filtrate was adjusted to pH 2.0 and then an equal volume of ethyl acetate was added to the filtrate with vigorous stirring and stand for 1 hour and then centrifuged. Ethyl acetate extracts were evaporated in vacuo and then the residue was dissolved in methanol. The 5 µl of methanol solution was injected to Hitach Model 655 sample injector. (ii) Isolation and purification:

The cultured broth (150 liters) was filtered with the aid of diatomaseous earth (6kg), The pH of the filtrate (100 liters) was adjusted to 2.0, and then the filtrate was passed through a SP-207 (10 liters) column, which was washed with water (50 liters) and eluted with methanol (25 liters). Active eluate fractions were concentrated in vacuo to a volume of 5 liters and adjusted to pH 2.0 with 6N HCl and then extracted with 10 liters of ethyl acetate. The extract was concentrated in vacuo. The resultant material was applied to a DEAE-TOYOPEARL 650C (1.0 liter). The column was washed with water (10 liters) and then eluted with 10 liters of 0.03M NaCl. The active fractions were combined and adjusted to pH 2.0 with 6N HCl. The solution was adsorbed on SP-207 (500 ml) and the active principal was eluted with methanol (2 liters). The desalted eluate was concentrated in vacuo to a volume of 200 ml. The solution was applied to pre-packed column (LiChroprep RP-18 size C, made by E. Merck) and eluted with 35% aqueous methanol in 0.1% trifluoroacetic acid solution. The active principal was eluted 90 minutes after the application of the sample. The eluate was concentrated in vacuo to remove methanol and then loaded onto a SP-207 column, again After washing the column with deionized water it was eluted with methanol. The active eluate was concentrated in vacuo to give FR901366 substance (100 mg) as pure white powders.

EXAMPLE 2

(i) Fermentation

A aqueous seed medium (100 ml) containing soluble starch (1%), sucrose (1%), glucose (1%), cotton seed flour (1%), peptone (0.5%), soybean meal (0.5%) and calcium carbonate (0.1%) was poured into each of ten 500 ml-Erlenmeyer flasks and sterilized at 120° C. for 30 minutes.

A loopful of slant culture of Streptomyces sp. No. 89009 (FERM BP-2474) was inoculated to each of the media and cultured at 30° C. for 3 days on a rotary shaker (220 rpm, 5.1 cm throw). The resultant first stage seed culture was transferred to a sterilized second stage seed of 200 liters of the seed medium supplemented silicone antifoam (0.1%) in a 500-liter jar fermentor. The second stage seed was cultured for 2 days at 30° C. with aeration at 200 liters per minute and stirring at 90 rpm.

The 60 liters of seed, prepared as above, was inoculated to 3,000 liters of a production medium containing sucrose (4%), peanut powder (1%), dried yeast (0.2%), wheat germ (0.5%), potato protein (0.5%) and silicon antifoam (0.1%). The fermentation ran for 7 days at 30° C. with aeration at 3,000 liters per minute and agitation at 90 rpm.

(ii) Isolation and Purification

The cultured broth was filtered with the aid of diatomaseous earth (50 kg), The pH of the filtrate (2,550 liters) was adjusted to 2.0, and then the filtrate was passed through a Diaion SP-207 (170 liters) column. The column was washed with water (1600 liters) and eluted with 50% aqueous methanol (800 liters) and methanol (440 liters).

The 50% aqueous methanol fraction was neutralized (pH 7.0) with 6N NaOH and then concentrated to about 20 liters in vacuo. This concentrate was washed with ethyl acetate (40 liters) and the extract was discarded. An aqueous layer was adjusted to pH 2.0 with 6N HCl and then extracted with 40 liters of ethyl acetate.

The remaining aqueous layer was extracted with n-butanol (20 liters). This extract containing FR901367 substance was concentrated to small volume and then diluted to 60 liters with water.

This solution was applied to DEAE-TOYOPEARL 650C (Cl⁻) (made by TOSOH CORP.) (12 liters). The column was washed with water (70 liters) and then eluted with 116 liters of 0.01M NaCl. The rich cut from DEAE-TOYOPEARL 650C separation was adsorbed to SP-207 (1 liter) to remove the salts. The resin was washed with water (10 liters), 25% aqueous methanol (4 liters) and 30% aqueous methanol (2 liters). The active principal was eluted with 50% aqueous methanol (4 liters) and 75% aqueous methanol (2 liters). The eluate was concentrated to a volume of 1.6 liters (pH 3).

This solution was rechromatographed on DEAE-TOYOPEARL 650C (330 ml). The column washed with water (900 ml) and 0.002M NaCl (900 ml), was eluted with 0.005M NaCl (900 ml) and 0.01 M NaCl (2400 ml). Active fractions were combined, adjusted to pH 2.1 with 1N HCl and then desalted by using SP-207 column (150 ml).

The eluate from SP-207 was concentrated to 10 ml, and then applied to pre-packed column (reverse-phase silica gel, Lichroprep RP-18, 43-62 µm, size C (made by E. Merck) equilibrated with 0.1% trifluoroacetic acid (TFA) solution. The reverse-phase silica gel was washed with 1,000 ml of the same solution and eluted with 18% acetonitrile in 0.1% TFA. The elution was monitered by UV at 230 nm. The required cuts were combined, concentrated to 200 ml and then loaded onto a SP-207 column (20 ml). After washing with water and 40% aqueous methanol, it was eluted 60% aqueous methanol and 70% aqueous methanol. The active eluate was concentrated in vacuo and weighed to give 337 mg of pure FR901367 substance.

EXAMPLE 3

FR901366 substance (1.3 g) and 1M Tris-HCl buffer (pH 7.4, 160 ml) were added to a culture broth (640 ml) of Pseudomonas cepacia No. 97, which was grown in a medium containing 1% glucose, 1% nutrient broth in water at 30° C. for 18 hours on a rotary shaker. The mixture was incubated at 37° C. for 52 hours with shaking. At this time, approximately 40% of FR901366 substance was converted to FR131132 substance. The mixture was diluted with methanol (800 Ml ) and filtered with an aid of diatomaseous earth (50 g). The filtrate was concentrated in vacuo, and the concentrate (400 ml) was acidified to pH 2.0 with 6N-hydrochloric acid and washed with ethyl acetate (400 ml) to remove remaining FR901366 substance. The aqueous layer was then put onto a column of Diaion SP-207 (50 ml). The column was washed with water (400 ml) and eluted with methanol (200 ml). The eluate was concentrated in vacuo and the residue was resolved in water (500 ml). The solution was acidified to pH 2.0 with 6N hydrochloric acid and applied to a pre-packed column of LiChroprep RP-18 (size C, made by E. Merck). The column was eluted with 13% aqueous acetonitrile containing 0.1% trifluoroacetic acid. Fractions containing object product were collected and concentrated to a half of volume in vacuo. The concentrate was then loaded onto a column of SP-207 (10 ml). The column was washed with water (100 ml) and eluted with methanol (50 ml). The eluate was concentrated to dryness in vacuo to give a white powder (280 mg) of FR131132 substance.

EXAMPLE 4

FR134851 substance (10 mg) was prepared in a similar manner to that of Example 3 from FR901367 substance (50 mg).

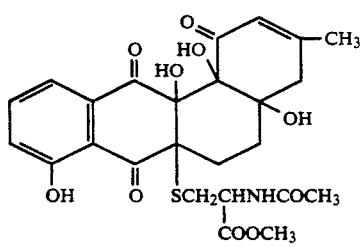

To a solution of FR901366 substance (100 mg) in methanol (10 ml) was added 10% trimethylsilyldiazomethane solution in n-hexane (0.5 ml) and the mixture was allowed to stand at ambient temperature for 30 minutes and then evaporated to dryness. The obtained oil was purified by preparative TLC [chloroform:methanol(95:5)] to give FR134624 substance (91 mg) as a colorless oil.

FAB-MS: m/z: 534 (M+H)+

$^1$H Nuclear magnetic resonance spectrum: (400 MHz, CDCl$_3$) δ: 11.26 (1H, s), 7.67 (1H, broad d, J=8 Hz), 7.58 (1H, dd, J=8 and 8 Hz), 7.24 (1H, broad d, J=8 Hz), 6.79 (1H, broad s), 6.13 (1H, broad d, J=8 Hz), 5.86 (1H, m), 5.77 (1H, broad s), 4.62 (1H, m), 4.49 (1H, broad s), 3.58 (3H, s), 2.91 (1H, broad d, J=18 Hz), 2.74 (1H, dd, J=13 and 5 Hz), 2.53 (1H, m), 2.49 (1H, dd, J=13 and 6 Hz), 2.20 (1H, m), 2.16 (1H, d, J=18 Hz), 1.97, (3H, s), 1.89 (1H, m), 1.82 (3H, s), 1.75 (1H, m)

EXAMPLE 6

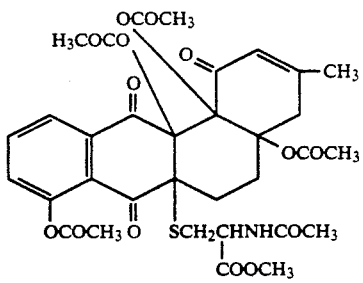

To a solution of FR134624 substance (85 mg) in pyridine (2 ml) containing 4-dimethylaminopyridine (1 mg) was added acetic anhydride (1 ml) and the mixture was allowed to stand at ambient temperature overnight. The mixture was concentrated to dryness. The residue was purified by preparative TLC [chloroform:methanol(97:3)] to afford FR134625 substance (67 mg) as a colorless oil.

FAB-MS: m/z: 724 (M+Na)+

$^1$H Nuclear magnetic resonance spectrum: (400 MHz, CDCl$_3$) δ: 8.01 (1H, broad d, J=8 Hz), 7.69 (1H, dd, J=8 and 8 Hz), 6.03 (1H, broad d, J=8 Hz), 5.98 (1H, m), 4.67 (1H, m), 3.65 (3H, s), 3.30 (1H, d, J=18 Hz), 2.86 (1H, m), 2.78 (1H, broad d), 2.56–2.48 (2H, m), 2.39 (3H, s), 2.37 (1H, m), 2.09 (3H, s), 2.03 (1H, m), 1.97 (3H, s), 1.89 (3H, s), 1.83 (3H, s), 1.82 (3H, s), 1.80 (1H, m).

EXAMPLE 7

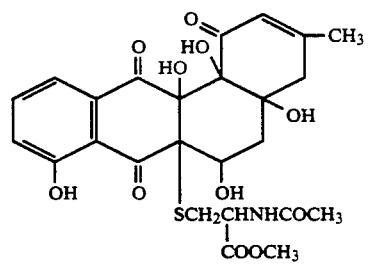

To a solution of FR901367 substance (15 mg) in methanol (3 ml) was added 10% trimethylsilyldiazomethane solution in n-hexane (0.1 ml) and the mixture was allowed to stand at ambient temperature for 15 minutes. The mixture was evaporated to dryness. The obtained oil was purified by preparative TLC [chloroform:methanol(9:1)] to give pure FR129795 substance (13 mg) as a colorless oil.

FAB-MS: m/z: 572 (M+Na)+

IR (CHCl$_3$): 3420, 3000, 1740, 1660, 1640, 1500, 1450, 1250, 200, 1160, 1120, 980 cm$^{-1}$.

$^1$H-NMR: (400 MHz, CDCl$_3$) δ: 11.09 (1H, s), 7.74 (1H, broad d, J=8 Hz), 7.67 (1H, dd, J=8 and 8 Hz), 7.30 (1H, broad d, J=8 Hz), 5.98 (1H, broad d, J=7 Hz), 5.90 (1H, m), 5.88 (1H, broad s), 5.61 (1H, broad s), 4.66 (1H, m), 4.57 (1H, m), 3.65 (3H, s), 2.96 (1H, broad d, J=18 Hz), 2.86 (1H, dd, J=13 and 4 Hz), 2.64–2.57 (2H, m), 2.25 (1H, d, J=18 Hz), 2.19 (1H, dd, J=16 and 2 Hz), 2.01 (3H, s), 1.88 (3H, s).

EXAMPLE 8

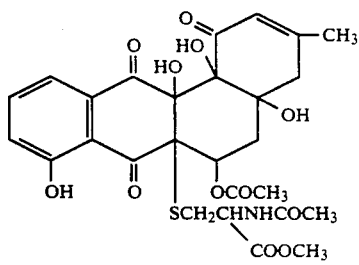

FR129797 substance:

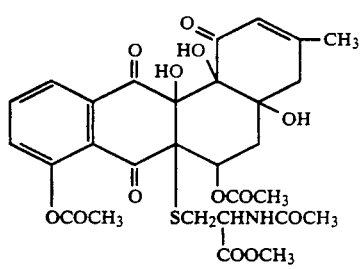

To a solution of FR129795 substance (10 mg) in methylene chloride (1 ml) were added acetic anhydride (0.02 ml) and pyridine (0.002 ml) and the mixture was allowed to stand at ambient temperature overnight. The mixture was concentrated in vacuo and the residue was purified by preparative TLC [chloroform:methanol(19:1)] to give FR129796 substance (7 mg) and FR129797 substance (3 mg).

FR129796 substance:
TLC [chloroform:methanol(9:1)]: Rf: 0.51.
FAB-MS m/z 592 (M+H)+
$^1$H Nuclear magnetic resonance spectrum: (400 MHz, CDCl$_3$) δ: 11.36 (1H, s), 7.77 (1H, broad d, J=8 Hz), 7.66 (1H, dd, J=8 and 8 Hz), 7.31 (1H, broad d, J=8 Hz), 5.95 (1H, m), 5.92 (1H, broad d, J=7 Hz), 5.90 (1H, broad s), 5.88 (1H, broad s), 5.52 (1H, t, J=3 Hz), 4.73 (1H, m), 3.70 (3H, s), 2.89 (1H, dd, J=13 and 4 Hz), 2.85 (1H, broad, J=18 Hz), 2.73 (1H, dd, J=13 and 5 Hz), 2.63 (1H, dd, J=16 and 4 Hz), 2.22 (1H, d, J=18 Hz), 2.16 (1H, dd, J=16 and 3 Hz), 2.08 (3H, s), 2.01 (3H, s), 1.89 (3H, s).

FR129797 substance:
TLC [chloroform:methanol(9:1)]: Rf: 0.47.
FAB-MS m/z 656 (M+Na)+
IR (CHCl$_3$): 3420, 3000, 1760, 1740, 1680, 1660, 1370, 1210 cm$^{-1}$.

$^1$H Nuclear magnetic resonance spectrum: (400 MHz, CDCl$_3$) δ: 8.18 (1H, broad d, J=8 Hz), 7.76 (1H, dd, J=8 and 8 Hz), 7.40 (1H, broad d, J=8 Hz), 6.03 (1H, broad s), 5.94 (1H, broad d, J=7 Hz), 5.92 (1H, m), 5.68 (1H, broad s), 5.50 (1H, t, J=3 Hz), 4.72 (1H, m), 3.73 (3H, s), 2.85 (1H, broad d, J=18 Hz), 2.74–2.70 (2H, m), 2.59 (1H, dd, J=15 and 4 Hz), 2.38 (3H, s), 2.20 (1H, d, J=18 Hz), 2.13 (1H, dd, J=15 and 3 Hz), 2.09 (3H, s), 2.01 (3H, s), 1.90 (3H, s).

EXAMPLE 9

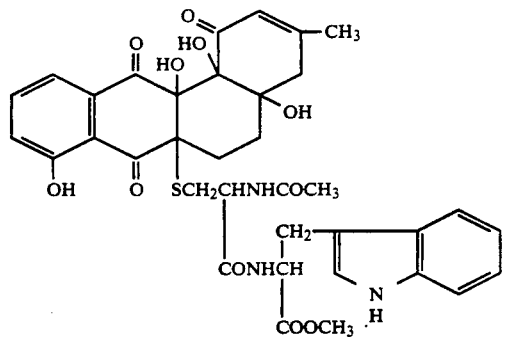

To a mixture of FR901366 substance (52 mg), L-tryptophane methyl ester hydrochloride (28 mg), N-hydroxybenzotiazole (15 mg) in N,N-dimethylformamide (5 ml) was added 1-ethyl-3-(3-dimethylaminopropyl)carbodiimide (20 mg) under ice-bath cooling. After being stirred for 2 hours at the same temperature, the mixture was allowed to stand for 15 hours at ambient temperature. The mixture was concentrated in vacuo and the residue was dissolved in ethyl acetate (10 ml). The solution was washed with 0.5 N hydrochloric acid (5 ml) and water (5 ml×2), dried over magnesium sulfate and evaporated in valuo. The residue was purified by preparative TLC (silica gel plate) and developed with a mixture of chloroform and methanol (10:1) to give FR134762 substance (42 mg).

TLC [silica gel plate, chloroform:methanol(10:1)]: Rf: 0.45 .
FAB-MS m/z: 720 (M+H)

EXAMPLE 10

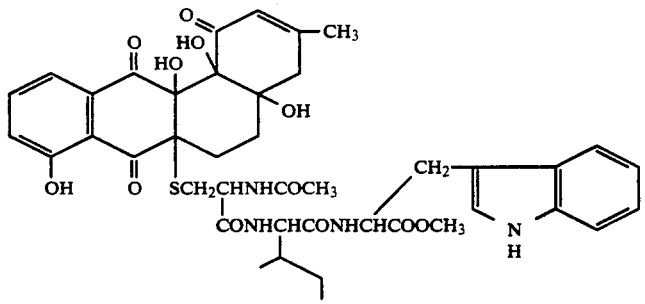

FR901366 substance (52 mg), L-isoleucyl-L-tryptophane methyl ester (35 mg), N-hydroxybenzotriazole (17 mg), and 1-ethyl-3-(3-dimethylaminopropyl)carbodiimide (20 mg) in N,N-dimethylformamide (2 ml) was reacted according to a similar manner to that of Example 9 to give FR134763 substance (37 mg).

TLC [silica gel plate, chloroform:methanol(10:1)]: Rf: 0.45.

FAB-MS: m/z: 833 (M+H)+

EXAMPLE 11

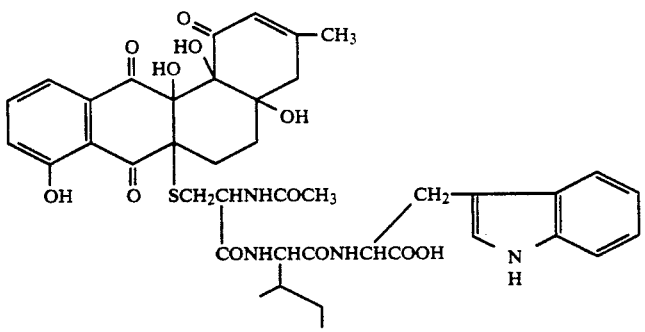

To a solution of FR134763 substance (15 mg) in methanol (1 ml) was added 1N sodium hydroxide solution (0.5 ml). After being stirred for 1 hour at ambient temperature, methanol was evaporated in vacuo. The concentrate was acidified with 1N-hydrochloric acid and extracted with ethyl acetate (15 ml), dried over magnesium sulfate and evaporated in vacuo to give FR134764 substance (10 mg).

TLC [silica gel plate, chloroform:methanol:acetic acid(8:1:1)]:
Rf: 0.2.
FAB-MS: m/z: 819 (M+H)+

EXAMPLE 12

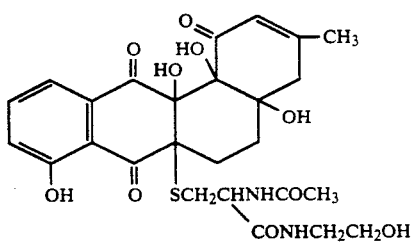

FR901366 substance (52 mg), ethanolamine (8 mg), N-hydroxybenzotiazole (17 mg), and 1-ethyl-3-(3-dimethylaminopropyl)carbodiimide (20 mg) in N,N-dimethylformamide (2 ml) was reacted according to a similar manner to that of Example 9 to give FR134761 substance (36 mg).

TLC [silica gel plate, chloroform:methanol:acetic acid(8:1:1)]:
Rf: 0.2.
FAB-MS: m/z: 563 (M+H)+

EXAMPLE 13

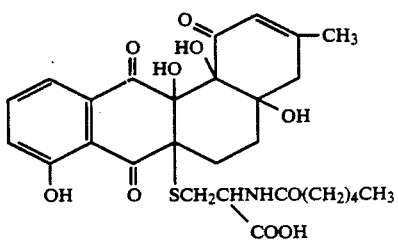

To a solution of FR131132 substance (15 mg) in a mixture of methanol (1 ml) and water (0.5 ml) was added 2.5% sodium dicarbonate aqueous solution and the pH of the mixture was adjusted to pH 8. n-Hexanoic acid N-hydroxysuccinimide ester (10 mg) was added to the mixture After being stirred for 5 hours at ambient temperature, methanol was concentrated in vacuo. The concentrate was acidified to pH 1 with 1N hydrochloric acid and extracted with ethyl acetate (10 ml). The extract was washed with saturated sodium chloride aqueous solution, dried over magnesium sulfate and evaporated in vacuo to give FR131668 substance (17 mg).

TLC [silica gel plate, chloroform:methanol:acetic acid(8:1:1)]:
Rf: 0.35.
FAB-MS: m/z: 576 (M+H)+

EXAMPLE 14

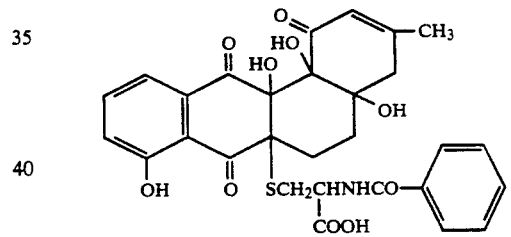

FR131132 substance (15 mg) and benzoic anhydride (10 mg) were reacted according to a similar manner to that of Example 13 to give FR131661 substance (16 mg).

TLC [silica gel plate, chloroform:methanol:acetic acid(8:1:1)]:
Rf: 0.26.
FAB-MS: m/z: 582 M+H)30

EXAMPLE 15

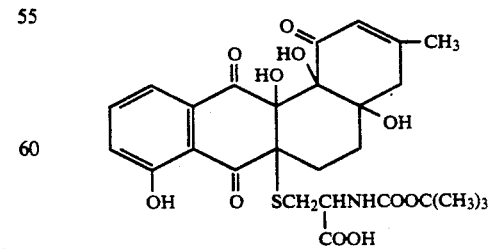

FR131132 substance (10 mg) and di-t-butyldicarbonate (10 mg) were reacted according to a similar manner to that of Example 13 to give FR131662 substance (12 mg).

TLC [silica gel plate, chloroform:methanol:acetic acid(8:1:1)]:
Rf: 0.38.
FAB-MS: m/z: 578 (M+H)+

EXAMPLE 16

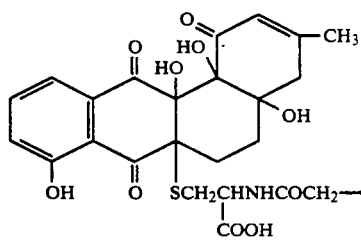

FR131132 substance (10 mg) and 4-chlorophenylacetic acid N-hydroxysuccinimide ester (10 mg) were reacted in a similar manner to that of Example 13 to give FR131663 substance (13 mg).
TLC [silica gel, chloroform:methanol:acetic acid(8:1:1)]:
Rf 0.27.
FAB-MS m/z 630 (M+H)+

EXAMPLE 17

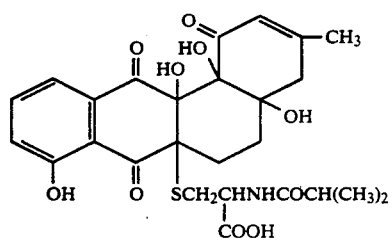

FR131132 substance (10 mg), isobutyric acid N-hydroxysuccinimide ester (5 mg) were reacted according to a similar manner to that of Example 13 to give FR131667 substance (7 mg).
TLC [silica gel plate, chloroform:methanol:acetic acid(8:1:1)]:
Rf: 0.23.
FAB-MS: m/z: 548 (M+H)+

What we claim is:
1. A compound of the formula:

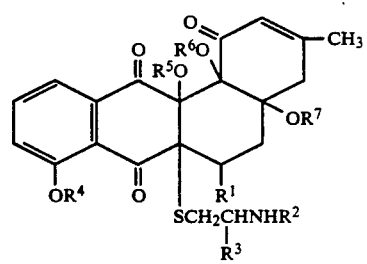

wherein
$R^1$ is hydrogen, hydroxy or acyloxy,
$R^2$ is hydrogen, or acyl,
$R^3$ is acyl,
$R^4$ is hydrogen or acyl,
$R^5$ is hydrogen or acyl,
$R^6$ is hydrogen or acyl, and $R^7$ is hydrogen or acyl,
or a pharmaceutically acceptable salt thereof.

2. A compound according to claim 1, which is FR901366 substance having the formula:

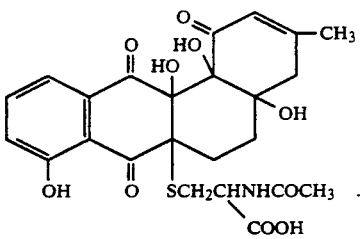

3. A compound according to claim 1, which is FR901367 substance having the formula

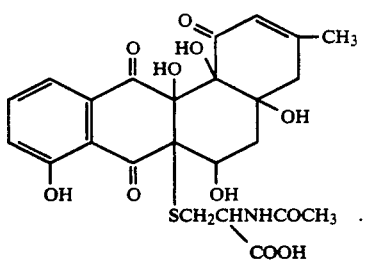

4. A pharmaceutical composition comprising a compound of claim 1, as an active ingredient, in association with a pharmaceutically acceptable, substantially nontoxic carrier or excipient.

5. A compound of claim 1, wherein $R^3$ is carboxy, $R^1$, $R^2$, $R^4$, $R^5$, $R^6$, and $R^7$ are hydrogen.

6. A compound of claim 1, wherein $R^1$ is hydroxy, $R^3$ is carboxy, $R^2$, $R^4$, $R^5$, $R^6$, and $R^7$ are hydrogen.

7. A compound of claim 1, wherein $R^1$ is hydroxy, $R^2$ is acetyl, $R^3$ is carbomethoxy, $R^4$, $R^5$, $R^6$, and $R^7$ are hydrogen.

8. A compound of claim 1, wherein $R^2$ is tertbutoxycarbonyl, $R^3$ is carboxy, $R^1$, $R^4$, $R^5$, and $R^6$, and $R^7$ are hydrogen.

9. A compound of claim 1, wherein $R^2$ is acetyl, $R^3$ is (2-hydroxyethyl)carbamyl, $R^1$, $R^4$, $R^5$, $R^6$, and $R^7$ are hydrogen.

10. A compound of claim 1, wherein $R^1$ is acetoxy, $R^2$ is acetyl, $R^3$ is carbomethoxy, $R^4$, $R^5$, $R^6$, and $R^7$ are hydrogen.

11. A compound of claim 1, wherein $R^2$ is acetyl, $R^3$ is (N-L-isoleucyl-L-tryptophan) carbamyl, $R^1$, $R^4$, $R^5$, $R^6$, and $R^7$ are hydrogen.

12. A compound of claim 1, wherein $R^1$ is acetoxy, $R^2$ is acetyl, $R^3$ is carbomethoxy, $R^4$ is acetyl, $R^5$, $R^6$, and $R^7$ are hydrogen.

13. A method for treating vasoconstrictive disorders in a patient in need of treatment, which comprises administering to said patient a vasodilating amount of a composition comprising a compound of the formula

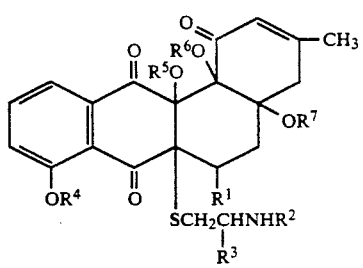
[I] wherein
R¹ is hydrogen, hydroxy or acyloxy,
R² is hydrogen, or acyl,
R³ is acyl,
R⁴ is hydrogen or acyl,
R⁵ is hydrogen or acyl,
R⁶ is hydrogen or acyl, and
R⁷ is hydrogen or acyl,
or a pharmaceutically acceptable salt thereof, in combination with a pharmaceutical carrier thereof.
* * * * *